(12) United States Patent
Burke et al.

(10) Patent No.: US 7,064,202 B1
(45) Date of Patent: *Jun. 20, 2006

(54) CAMPTOTHECIN INTERMEDIATES AND PRODRUGS AND METHODS OF PREPARATION THEREOF

(75) Inventors: Thomas G. Burke, deceased, late of Lexington, KY (US); Dennis P. Curran, Pittsburgh, PA (US); Wu Du, San Diego, CA (US)

(73) Assignees: University of Kentucky Research Foundation, Lexington, KY (US); University of Pittsburgh, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/843,821

(22) Filed: May 12, 2004

Related U.S. Application Data

(60) Provisional application No. 60/469,754, filed on May 12, 2003.

(51) Int. Cl.
*C07D 413/04* (2006.01)
*C07D 487/12* (2006.01)
(52) U.S. Cl. ........................ 544/125; 546/70
(58) Field of Classification Search ........... 544/125; 546/70
See application file for complete search history.

(56) References Cited

U.S. PATENT DOCUMENTS

| | | |
|---|---|---|
| 5,552,156 A | 9/1996 | Burke |
| 5,736,156 A | 4/1998 | Burke |
| 6,136,978 A | 10/2000 | Curran et al. |
| 6,207,832 B1 | 3/2001 | Curran et al. |
| 6,291,676 B1 | 9/2001 | Burke et al. |
| 6,376,676 B1 | 4/2002 | Curran et al. |
| 6,410,731 B1 | 6/2002 | Currant et al. |
| 6,743,917 B1 | 6/2004 | Curran et al. |

FOREIGN PATENT DOCUMENTS

WO    WO 9207856 A1  *  5/1992

OTHER PUBLICATIONS

Liu X. et al. Versatile Prodrug Approach for Liposomal Core-Loading of Water-Insoluble Camptothecin Anticancer Drugs, J. Amer. Chem. Soc., 124(26), pp. 7650-7651 (2002).*
Joisen, H., 7-Silylcamptothecins (Silatecans): A New Family of Camptothecin Antitumor Agents, Bioorg. Med. Chem. Lett., 7(24), pp. 3189-3194 (1997).*
Liu, Xinli et al., A Versatile Prodrug Approach for Liposomal Core-Loading of Water-Insoluble Camptothecin Anticancer Drugs; J. Am. Chem. Soc.; Jan. 16, 2002, 124, 7650-7651.
Curran, D.P., Liu, H.; Josien, H; Ko, S.B., Tandem Radical Reactions of Isonitriles with 2-Pyridonyl and other aryl adicals: Scope and Limitations, and a First Generation Synthesis of (+/−)-Camptothecin, Tetrahedron, 52, 11385-11404 (1996). Published Aug. 1996.
Palmisano, F. et al., Determination of Methotrexate in Untreated Body Fluids by Micellar Liquid Chromatography, Anal. Chem., May 1989, (61) 946-950.
Pinnaduwage, P. et al. Stable Target-Sensitive Immunoliposomes, Biochemistry, 32, pp. 2850-2855 1992.
Mi, Z. and Burke, T.G., Differential Interactions of Camptothecin Lactone and Carboxylate Forms with Human Blood Components, Biochemistry, 33, 10325-10336 (1994).
Mi, Z. and Burke, T.G., Marked Interspecies Variations Concerning the Interactions of Camptothecin with Serum Albumins: A Frequency-Domain Fluorescence Spectroscopic Study, Biochemistry, 33, 12540-12545 (1994).
Mi, Z. et al., Reduced Albumin Binding Promotes the Stability and Activity of Topotecan in Human Blood, Biochemistry, 34, 13722-13727 (1995).
Josien, H. et al., 7-Silylcamptothecins (Silatecans): A New Family of Camptothecin Antitumor Agents, Bioorg. Med. Chem. Lett. vol. 7, No. 24, 3189-3295 (1997).
Josien, H. et al., A General Synthetic Approach to the (20S)-Camptothecin Family of Antitumor Agents by a Regiocontrolled Cascade Radical Cyclization of Aryl Isonitriles, Chem. Eur. J. 4, 67-83 (1998).
Curran, D.P. et al., New 4+1 Radical Annulations: A Formal Total Synthesis of (+/−)-Camptothecin, J. Am. Chem Soc., 114, 5863-5864 (1992).
Burke, T. et al., Liposomal Stabilization of Camptothecin's Lactone Ring, J. Am. Chem. Soc., 114, 8318-8319 (1992).
Margali, R. et al., Liposomal Drug Delivery: Thermodynamic and Chemical Kinetic Considerations, J. Controlled Release, vol. 17, 285-296 (1991).
Akhtar, et al., Liposome delivery of Antisense Oligonucleotides: Adsorption and Efflux characteristics of Phosphorothioate Oligodeoxynucleotides, J. Controlled Release 22 (1992) 47-56.
Hong, C. et al., Nucleoside Conjugates. 11. Synthesis and Antitumor Activity of 1- -D-Arabinofuranosylcytosine and Cytidine Conjugates of Thioether Lipids, J. Med. Chem., 1990, 33, 1380-1386.
Burke, T.G. et al., The Structural Basis of Camptothecin Interactions with Human Serum Albumin: Impact on Drug Stability, J. Med. Chem., 37, 40-46 (1994).
Bom, D. et al., Novel A,B,E-Ring-Modified Camptothecins Displaying High Lipophilicity and Marked Improved Human Blood Stabilities, J. Med. Chem. 42, 3018-3022, 1999.

(Continued)

*Primary Examiner*—Kamal A. Saeed
*Assistant Examiner*—Nyeemah Grazier
(74) *Attorney, Agent, or Firm*—King & Schickli, PLLC

(57) ABSTRACT

The present invention relates to novel intermediates and prodrugs of camptothecin and related analogs.

2 Claims, No Drawings

OTHER PUBLICATIONS

Killon, J. et al., Augmentation of Antiproliferative Activity of Interferon Alfa Against Human Bladder Tumor Cell Lines by Encapsulation of Interferon Alfa Within Liposomes, J. Natl. Cancer Inst. 81, 1387-1392 (1989).

Rahman, A. et al., Anti-Laminin Receptor Antibody Targeting of Liposomes with Encapsulated Doxorubicin to Human Breast Cancer Cells in Vitro, J. Natl. Cancer Inst. 81, 1794-1800 (1989).

Burris, H. et al. Activity of Topotecan, a New Topoisomerase I Inhibitor, Against Human Tumor Colony-Forming Units In Vitro, J. Natl. Cancer Inst. 84, 1816-1820 (1992).

Jett, M. et al., Tumoricidal Effects of Liposomes Containing Phosphatidylinositol or Phosphatidylcholine, Methods in Enzymology, vol. 141, pp. 459-466 (1987).

Woodle, M. et al., Liposome Preparation and Size Characterization, Methods in Enzymology, vol. 171, pp. 193-217 (1989).

Szoka, F. et al., Procedure for Preparation of Liposomes with Large Internal Aqueous Space and High Capture by Reverse-Phase Evaporation, Proc. Nat. Acad. Sci., vol. 75, 4194-4198. (Sep. 1978).

Gabizon, A. et al., Liposome Formulations with Prolonged Circulation Time in Blood and Enhanced Uptake by Tumors, Proc. Natl. Acad. Sci. 85, 6949-6953, Sep. 1988.

Papahadjopoulos et al., Sterically Stabilized Liposomes: Improvements in Pharmacokinetics and Antitumor Therapeutic Efficacy, Proc. Natl. Acad. Sci. 88, 11460-11464, Dec. 1991.

Shelly, K. et al., Model Studies Directed Toward the Boron Neutron-Capture Therapy of Cancer: Boron Delivery to Murine Tumors with Liposomes, Proc. Natl. Acad. Sci. vol. 89, 9039-9043, Oct. 1992.

Giovanella, B. et al., DNA Topoisomerase I-Targeted Chemotherapy of Human Colon Cancer in Xenografts, Science 246, 1046-1048, Nov. 24, 1989.

Josien, H. et al, Synthesis of (S)-Mappicine and Mappicine Ketone Via Radical Cascade Reaction of Isonitriles, Tetrahedron, 53, 8881-8886 (1997).

Jew et al., Synthesis and Antitumor Activity of 7-Substituted 20(RS)-Camptothecin Analogues, Bioorg. Med. Chem. Letters 6, 845-848.

Wang et al., Synthesis of Novel Water-Soluble 7-(aminoacylhydrazono) -formyl Camptothecins with Potent Inhibition of DNA Topo. I, Bioorg. Med. Chem. 2(12), 1397-1402 (1994).

Wang et al., Novel Water-Soluble 7-(acylhydrazono) -formyl Camptothecins as Potent Inhibitors of DNA Topo. I, Bioorg. Med. Chem. Lett. 4(4), 579-582 (1994).

Sawada et al., Chem. Mod. of an Antitumor Alkaloid Camptothecin: Synthesis and Antitumor Activity of 7-C-Sub. Camptothecs; Chem. Pharm. Bull. 39(10), 2574-80(1991).

* cited by examiner

CAMPTOTHECIN INTERMEDIATES AND PRODRUGS AND METHODS OF PREPARATION THEREOF

This application claims the benefit of U.S. Provisional Patent Application Ser. No. 60/469,754 filed on May 12, 2003.

This invention was made with Government support under NIH Grant Number 1R01CA63653. The Government may have certain rights in this invention.

TECHNICAL FIELD

The present invention relates to novel intermediates and prodrugs of camptothecins.

BACKGROUND OF THE INVENTION

The anticancer agent camptothecin and related compounds (FIG. 1) are emerging as an important class of agents useful in the treatment of cancer.

FIG. 1. Clinical candidates and FDA-approved analogs in the camptothecin family of antitumor agents These agents display a unique mechanism of action: stabilization of the covalent binding of the enzyme topoisomerase I (topo I), an intranuclear enzyme that is overexpressed in a variety of tumor lines, to DNA. This drug/enzyme/DNA complex leads to reversible, single strand nicks which, according to the fork collision model, promote irreversible and lethal double strand DNA breaks during replication.

The camptothecin class of anticancer agents have exhibited unusual reactivity in vivo, both with respect to drug hydrolysis and blood protein interactions. These factors have hindered the pharmaceutical development and clinical implementation of camptothecins. In terms of hydrolysis, each of the camptothecins shown in FIG. 1 contains an α-hydroxy-δ-lactone pharmacophore. At physiological pH of 7 and above this functionality is reactive, readily converting to the biologically inactive "ring opened" carboxylate form. Thus, as a result of the labile α-hydroxy-δ-lactone pharmacophore, an equilibrium is established between two distinct drug species: 1) the biologically active lactone form where the lactone ring remains closed; and 2) a biologically-inactive carboxylate form generated upon the hydrolysis of the lactone ring of the parent drug. In this invention we describe novel intermediates and prodrugs of camptothecin and related analogs.

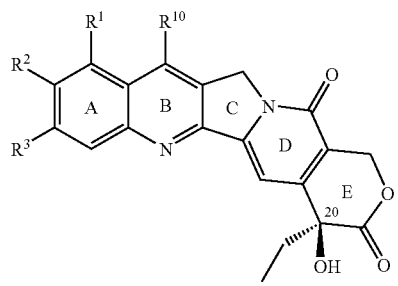

| Aqueous Solubility | Compound | $R^{10}$ | $R^1$ | $R^2$ | $R^3$ |
|---|---|---|---|---|---|
| Soluble | Topotecan/TPT | H | $CH_2NH(CH_3)_2$ | OH | H |
| " | CDK602 | H | $C_2H_5NHCH(CH_3)_2$ | H | H |
| " | Irinotecan/CPT-11 | $C_2H_5$ | H | [piperidino-piperidine carbonyloxy] | H |
| " | GI-147211C/GG-211 | $-CH_2-N\text{(4-methylpiperazinyl)}-CH_3$ | H | | [1,3-dioxolane] |
| Insoluble | Camptothecin | H | H | H | H |
| " | 9-AC | H | $NH_2$ | H | H |
| " | 9-NC/Rubitecan | H | $NO_2$ | H | H |
| " | SN-38 | $C_2H_5$ | H | OH | H |
| " | DB-67 | $Si(CH_3)_2C(CH_3)_3$ | H | OH | H |
| " | MDCPT | H | H | | [1,3-dioxolane] |

DETAILED DESCRIPTION OF THE INVENTION

The invention includes camptothecin lactam intermediates with the following structure A:

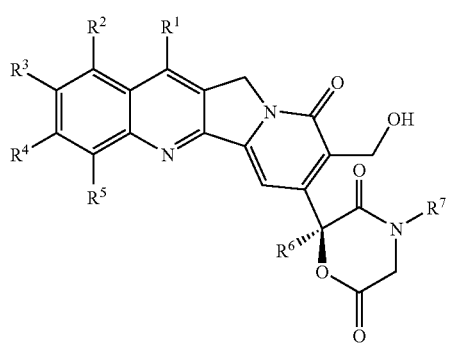

where $R^1$ may be: a) hydrogen, a halogen atom, a branched or linear alkyl group, a branched or linear alkenyl group, a branched or linear alkynyl group, a cycloalkyl group, a cycloalkenyl group, an alkoxy group, an alkylamino group, a dialkylamino group, an alkylthiol group, a thiol group, a phenyl group, an amino group, a nitro group, a cyano group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate; c) $R^8$, $R^9$ and the nitrogen to which they are attached may be taken together to form a saturated or unsaturated three to ten membered heterocyclic ring which may contain O, S, $NR^{10}$ where $R^{10}$ is hydrogen, an alkyl group, an alkenyl group, an alkynyl group, an alkoxy group or a carbamate; d) $R^1$ may be linked to $R^2$ as $R^1(CH_2)_Q R^2$ wherein Q represents an integer 1–10, additionally this ring may contain one or more NH, O or S atoms in place of one or more —$CH_2$— groups;

$R^2$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group; b) a $(CH_2)_Y NR^8$, $R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate; c.) $R^8$, $R^9$ and the nitrogen to which they are attached may be taken together to form a saturated or unsaturated three to ten membered heterocyclic ring; d) $R^2$ may be linked to $R^3$ as $R^2(CH_2)_G R^3$ wherein G may be an integer from 1–10, additionally this ring may contain one or more NH, O or S atoms in place of one or more —$CH_2$— groups;

$R^3$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group, a hydroxyl group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate; c) $R^8$, $R^9$ and the nitrogen to which they are attached may be taken together to form a saturated or unsaturated three to ten membered heterocyclic ring; d) $R^3$ may be linked to $R^4$ as $R^3(CH_2)_G R^4$ wherein G may be an integer from 1–10, additionally this ring may contain one or more NH, O or S atoms in place of one or more —$CH_2$— groups;

$R^4$ may be hydrogen, a halogen atom, a hydroxy group, an amino group, a methoxy group, an alkyl group, an alkynyl group or an alkenyl group;

$R^5$ may be hydrogen or fluorine;

$R^6$ may be an alkyl group, an alkenyl group, an alkynyl group, or a benzyl group;

$R^7$ may be hydrogen, an alkyl group, an alkenyl group, an alkynyl group, a benzyl group, an alkoxy group, an aryloxy group, or an acyloxy group; and pharmaceutically acceptable salts thereof.

The invention includes camptothecin ortho lactone intermediates and prodrugs with the following structure B:

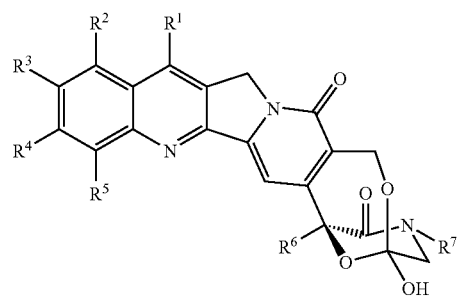

where $R^1$ may be: a) hydrogen, a halogen atom, a branched or linear alkyl group, a branched or linear alkenyl group, a branched or linear alkynyl group, a cycloalkyl group, a cycloalkenyl group, an alkoxy group, an alkylamino group, a dialkylamino group, an alkylthiol group, a thiol group, a phenyl group, an amino group, a nitro group, a cyano group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate; c) $R^8$, $R^9$ and the nitrogen to which they are attached may be taken together to form a saturated or unsaturated three to ten membered heterocyclic ring which may contain O, S, $NR^{10}$ where $R^{10}$ is hydrogen, an alkyl group, an alkenyl group, an alkynyl group, an alkoxy group or a carbamate; d) $R^1$ may be linked to $R^2$ as $R^1(CH_2)_Q R^2$ wherein Q represents an integer 1–10, additionally, this ring may contain one or more NH, O or S atoms in place of one or more —$CH_2$— groups;

$R^2$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate; c) $R^8$, $R^9$ and the nitrogen to which they are attached may be taken together to form a saturated or unsaturated three to ten membered heterocyclic ring; d) $R^2$ may be linked to $R^3$ as $R^2(CH_2)_G R^3$ wherein G may be an integer from 1–10, additionally this ring may contain one or more NH, O or S atoms in place of one or more —CH$_2$— groups;

$R^3$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group, a hydroxyl group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate c) $R^8$, $R^9$ and the nitrogen to which they are attached may be taken together to form a saturated or unsaturated three to ten membered heterocyclic ring; d) $R^3$ may be linked to $R^4$ as $R^3(CH_2)_G R^4$ wherein G may be an integer from 1–10, additionally this ring may contain one or more NH, O or S atoms in place of one or more —CH$_2$— groups;

$R^4$ may be hydrogen, a halogen atom, a hydroxy group, an amino group, a methoxy group, an alkyl group, an alkynyl group or an alkenyl group;

$R^5$ may be hydrogen or fluorine;

$R^6$ may be an alkyl group, an alkenyl group, an alkynyl group, or a benzyl group; and $R^7$ may be hydrogen, an alkyl group, an alkenyl group, an alkynyl group, a benzyl group, an alkoxy group, an aryloxy group, or an acyloxy group; and pharmaceutically acceptable salts thereof.

The invention also includes camptothecin intermediates and prodrugs with the following structure C:

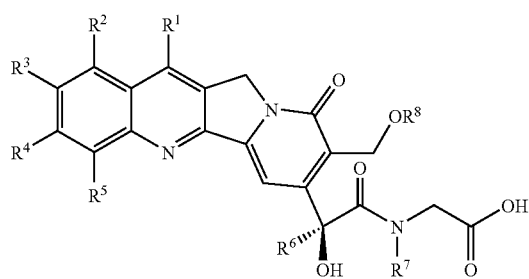

where $R^1$ may be: a) hydrogen, a halogen atom, a branched or linear alkyl group, a branched or linear alkenyl group, a branched or linear alkynyl group, a cycloalkyl group, a cycloalkenyl group, an alkoxy group, an alkylamino group, a dialkylamino group, an alkylthiol group, a thiol group, a phenyl group, an amino group, a nitro group, a cyano group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate; or c) $R^8$, $R^9$ and the nitrogen to which they are attached may be taken together to form a saturated or unsaturated three to ten membered heterocyclic ring which may contain O, S, $NR^{10}$ where $R^{10}$ is hydrogen, an alkyl group, an alkenyl group, an alkynyl group, an alkoxy group or a carbamate; d) $R^1$ may be linked to $R^2$ as $R^1(CH_2)_Q R^2$ wherein Q represents an integer 1–10, additionally this ring may contain one or more NH, O or S atoms in place of one or more —CH$_2$— groups;

$R^2$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate; c) $R^8$, $R^9$ and the nitrogen to which they are attached may be taken together to form a saturated or unsaturated three to ten membered heterocyclic ring; d) $R^2$ may be linked to $R^3$ as $R^2(CH_2)_G R^3$ wherein G may be an integer from 1–10, additionally this ring may contain one or more NH, O or S atoms in place of one or more —CH$_2$— groups;

$R^3$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group, a hydroxyl group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate c) $R^8$, $R^9$ and the nitrogen to which they are attached may be taken together to form a saturated or unsaturated three to ten membered heterocyclic ring; d) $R^3$ may be linked to $R^4$ as $R^3(CH_2)_G R^4$ wherein G may be an integer from 1–10, additionally this ring may contain one or more NH, O or S atoms in place of one or more —CH$_2$— groups;

$R^4$ may be hydrogen, a halogen atom, a hydroxy group, an amino group, a methoxy group, an alkyl group, an alkynyl group or an alkenyl group;

$R^5$ may be hydrogen or fluorine;

$R^6$ may be an alkyl group, an alkenyl group, an alkynyl group, a benzyl group, an alkoxy group, an aryloxy group, or an acyloxy group;

$R^7$ may be hydrogen, an alkyl group, an alkenyl group, a benzyl group, an alkoxy group, an aryloxy group, or an acyloxy group; and $R^8$ may be hydrogen, an alkyl group, or an alkenyl group; and pharmaceutically acceptable salts thereof.

All compounds of the present invention including the β-hydroxylactone group can exist in racemic form, enantiomerically enriched from, and enantiomerically pure form. The formulas of such compounds as set forth herein cover and/or include each such form.

The terms "alkyl", "aryl" and other groups refer generally to both unsubstituted and substituted groups unless specified to the contrary. Unless otherwise specified, alkyl groups are hydrocarbon groups and are preferably $C_1$–$C_{15}$ (that is, having 1 to 15 carbon atoms) alkyl groups, and more preferably $C_1$–$C_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or napthyl. As used herein, the terms "halogen" or "halo" refer to fluoro, chloro, bromo and iodo.

The term "alkoxy" refers to —$OR^d$, wherein $R^d$ is an alkyl group. The term "aryloxy" refers to —$OR^e$, wherein $R^e$ is an aryl group. The term acyl refers to —$C(O)R^f$. The term "alkenyl" refers to a straight or branched chain hydrocarbon group with at least one double bond, preferably with 2–15 carbon atoms, and more preferably with 2–10 carbon atoms (for example, —CH=$CHR^g$ or —$CH_2CH$=$CHR^g$). The term "alkynyl" refers to a straight or branched chain hydrocarbon group with at least one triple bond, preferably with 2–15 carbon atoms, and more preferably with 2–10 carbon atoms (for example, —C≡$CR^h$ or —$CH_2C$≡$CR^h$). The terms "alkylene," "alkenylene" and "alkynylene" refer to bivalent forms of alkyl, alkenyl and alkynyl groups, respectively.

The groups set forth above, can be substituted with a wide variety of substituents to synthesize homocamptothecin analogs retaining activity. For example, alkyl groups may preferably be substituted with a group or groups including, but not limited to, a benzyl group, a phenyl group, an alkoxy group, a hydroxy group, an amino group (including, for example, free amino groups, alkylamino, dialkylamino groups and arylamino groups), an alkenyl group, an alkynyl group and an acyloxy group. In the case of amino groups (—$NR^aR^b$), $R^a$ and $R_b$ are preferably independently hydrogen, an acyl group, an alkyl group, or an aryl group. Acyl groups may preferably be substituted with (that is, $R^f$ is) an alkyl group, a haloalkyl group (for example, a perfluoroalkyl group), an alkoxy group, an amino group and a hydroxy group. Alkynyl groups and alkenyl groups may preferably be substituted with (that is, $R^g$ and $R^h$ are preferably) a group or groups including, but not limited to, an alkyl group, an alkoxyalkyl group, an amino alkyl group and a benzyl group.

The term "acyloxy" as used herein refers to the group —$OC(O)R^d$.

The term "alkoxycarbonyloxy" as used herein refers to the group —$OC(O)OR^d$.

The term "carbamoyloxy" as used herein refers to the group —$OC(O)NR^aR^b$.

Amino and hydroxy groups may include protective groups as known in the art. Preferred protective groups for amino groups include tert-butyloxycarbonyl, formyl, acetyl, benzyl, p-methoxybenzyloxycarbonyl, trityl. Other suitable protecting groups as known to those skilled in the art are disclosed in Greene, T., Wuts, P. G. M., *Protective Groups in Organic Synthesis*, Wiley (1991), the disclosure of which is incorporated herein by reference.

In general, $R^1$, $R^2$ and $R^3$ are preferably not excessively bulky to maintain activity of the resultant camptothecin analog. Preferably, therefore, $R^1$, $R^2$ and $R^3$ independently have a molecular weight less than approximately 250. More preferably $R^1$, $R^2$ and $R^3$ independently have a molecular weight less than approximately 200.

Some of the camptothecin analogs of the present invention can be prepared for pharmaceutical use as salts with inorganic acids such as, but not limited to, hydrochloride, hydrobromide, sulfate, phosphate, and nitrate. The camptothecin analogs can also be prepared as salts with organic acids such as, but not limited to, acetate, tartrate, fumarate, succinate, citrate, methanesulfonate, p-toluenesulfonate, and stearate. Other acids can be used as intermediates in the preparation of the compounds of the present invention and their pharmaceutically acceptable salts.

For purification, administration or other purposes, the E-ring (the lactone ring) may be opened with alkali metal such as, but not limited to, sodium hydroxide or calcium hydroxide, to form opened E-ring analogs of compounds of structures A, B and C. The intermediates thus obtained are more soluble in water and may be purified to produce, after treatment with an acid, a purified form of the camptothecin analogs of the present invention.

All the novel compounds of the present invention whether in racemic, enantiomerically enriched or enantiomerically pure form display good biological activity while also possessing favorable characteristics for active loading into liposomal particle drug delivery systems of the micelle type disclosed and described in U.S. Pat. Nos. 5,316,771; 5,552,156 and 5,736,156. Pre-made liposomes can be efficiently loaded with any of the novel compounds of structures A, B and C of this invention using pH gradients.

In brief, in the active core loading process an amine-containing agent is loaded into the particle. For example, a gradient created by ammonia gas diffusing out of the liposome particle can result in diffusion or active loading of the compound/agent of the present invention inward to the core of the particle. The chemical gradient across the membrane creates a driving force for the compound/agent to replace the lost $NH_3$ from the interior of the liposome. Once inside the acidic confines of the core, the compound/agent becomes protonated and remains within the core, as its positive charge impedes retro-diffusion across the liposome bilayer. The protonated amine also prevents the occurrence of nucleophilic attack of the amine on the lactone carbonyl. As liposomes can be actively and/or passively targeted to the tumor, the liposome encapsulated compound/agent can be effectively concentrated at the tumor site, therby reducing exposure of the healthy host tissues to the cytotoxic agent yet enhancing exposure at the tumor target.

The tumor targeted approach involving liposomal delivery of core loaded compound/agent addresses multiple clinical issues. For example, reduced systemic toxicity can be achieved. Enhanced exposure at the tumor site in terms of relative amounts of drug reaching the tumor can also be achieved. Furthermore, enhanced exposure at the tumor site can be achieved in terms of prolonging the exposure of drug there.

The present invention also provides a method of treating a patient, which comprises administering a pharmaceutically effective amount of a compound of structures A, B and/or C or a pharmaceutically acceptable salt thereof. The compound may, for example, be administered to a patient afflicted with cancer and/or leukemia. The compounds of the present invention may also act as antiviral (for example, anti-HIV) agents and antiparasitic agents. The pharmaceutically effective amount or dosage is preferably between 0.01 to 80 mg of one of the compounds of structures A, B and/or C per kg of body weight. More preferably, the pharmaceutically effective amount or dosage is preferably between 0.1 to 40 mg of one of the compounds of structures A, B and/or C per kg of body weight. In general, a pharmaceutically effective amount or dosage contains an amount of one of the compounds of structures A, B and/or C effective to display antileukemic and/or antitumor (anticancer) behavior. Pharmaceutical compositions containing as an active ingredient of one of the compounds of structures A, B and/or C or a pharmaceutically acceptable salt thereof in association with a pharmaceutically acceptable carrier or diluent are also within the scope of the present invention.

The compounds of the present invention may be administered as a pharmaceutical composition containing the compounds and a pharmaceutically acceptable carrier or diluent. The compounds can also be administered as their ring open salt forms, since relactonization to their active forms can occur in the body (especially at sites of reduced pH). The active material can also be mixed with other active materials which do not impair the desired action and/or supplement the desired action. The compounds/active materials according to the present invention can be administered by any route, for example, orally, nasally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water: for injection, suspensions of liposomal particles whereby the particles contain stable, active drug within the core of the particle in a pH controlled and protected environment or associated to the outside of the particle or any of the bilayers of the particle, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. They may be enclosed in gelatin capsules or compressed into tablet. For the purpose of oral therapeutic administration, the aforesaid compounds may be incorporated with excipients and used in the form of tablets, troches, capsules, elixirs, suspensions, syrups, wafers, chewing gums and the like.

The tablets, pills, capsules and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such a colloidal silicon dioxide; and a sweetening agent such as sucrose or saccharin or flavoring agent such as peppermint, methyl salicylate, or orange flavoring may be added. When the dosage unit is in the form of a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and coloring and flavors. Materials used in preparing these various compositions should be pharmaceutically or veterinarally pure and non-toxic in the amount used.

The following examples are presented to further illustrate the invention, but it is not to be considered as limited thereto.

EXAMPLE 1

Preparation of camptothecin and SN-38 20(S) (ω-aminoalkanoanic esters

Camptothecin-20(S) (ω-aminoalkanoanic esters were synthesized by a procedure described by Wall and Wani et al., with novel modifications.

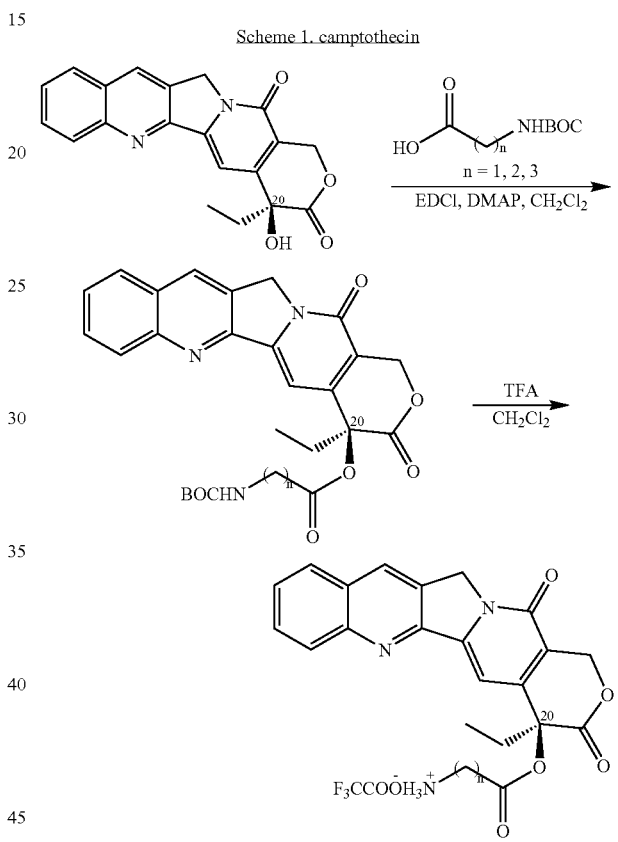

SN-38 ω-aminoalkanoanic esters, because of the presence of a 10-hydroxy group in addition to the 20(S)—OH, were synthesized by a novel procedure.

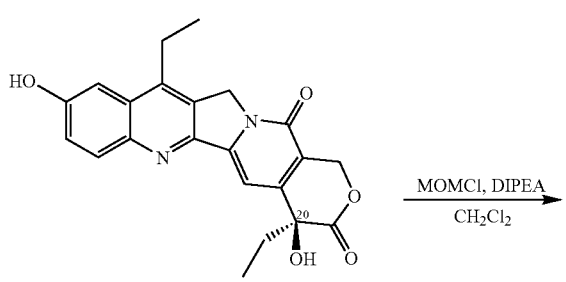

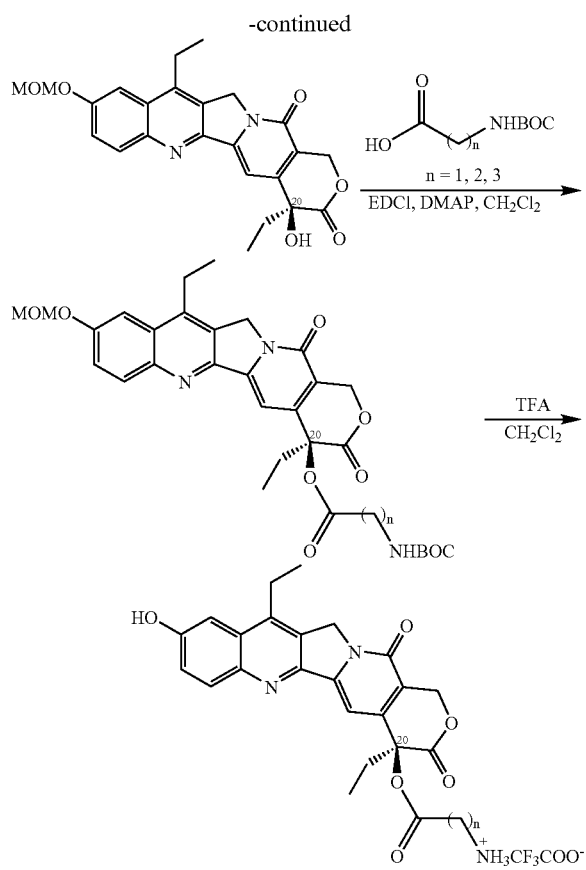

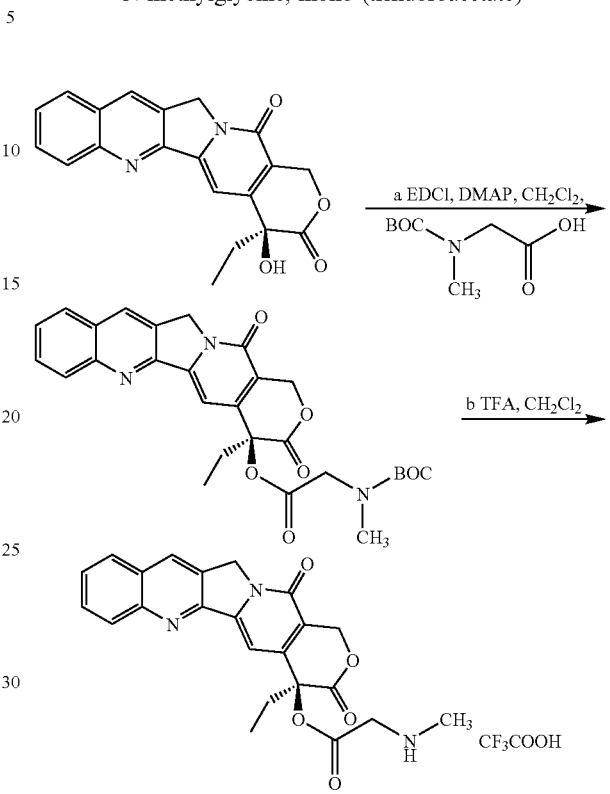

EXAMPLE 2

Synthesis of camptothecin-20-O-ester of N-methylglycine, mono (trifluoroacetate)

Briefly, SN-38 (1 equiv) was dissolved in anhydrous dichloromethane, and diisopropyl ethyl amine (DIPEA) (5 equiv) was added under nitrogen atmosphere. The reaction mixture was stirred for 10 min at room temperature followed by the addition of methoxylmethylchloride (MOMCl) (5 equiv). The resulting solution was left stirring overnight. The reaction was terminated. Then the reaction mixture was diluted by dichloromethane and washed several times with water, dried (MgSO$_4$), filtered, and concentrated. Purification by chromatography on silica gel gave 10-MOM protected compound.

1-Ethyl-3-(3-dimethylaminopropyl)carbodiimide (EDCI, 3 equiv) was slowly added to a solution of 10-MOM protected compound (1 equiv), tert-butoxycarbonylamino acid (3equiv) and 4-(dimethylamino)pyridine (DMAP, 0.6 equiv) and anhydrous dichloromethane, which had been precooled to 0° C. The resulting solution was allowed to warm to room temperature and stirred overnight. The organic fraction was washed with HCl (0.1 N) and water and then extracted several times with CH$_2$Cl$_2$. Organic layers were combined and dried with MgSO$_4$, followed by filtration and concentration. Purification of this residue by flash chromatography on silica gel gave chloromethyl methyl ether (MOM) and N-BOC protected prodrug. Deprotection of MOM and N-BOC groups was achieved simultaneously by stirring MOM and N-BOC protected prodrug in dichloromethane and trifluoracetic acid for 30 minutes at room temperature, followed by concentration under high vacuum and recrystalization in methanol and ethyl ether. Purity of final products was determined by HPLC and prodrug purity was found to be greater than 98% pure.

A solution of camptothecin (100 mg, 0.29 mmol), N-(tert-butoxycarbonyl)metylyglycine (136 mg, 0.72 mmol) and DMAP(14 mg, 0.12 mmol) in 10 ml anhyd. dichloromethane was cooled to 0° C., followed by the addition of EDCI(110 mg, 0.57 mmol). The reaction mixture was allowed to come to room temperature and stirred overnight. The resulting solution was washed with HCl (5 ml, 0.1 N) and water, then extracted with dichloromethane. The organic layer was dried with MgSO$_4$, then filtered and concentrated. Purification by column chromatography on silica gel (CH$_2$Cl$_2$–CH$_3$COCH$_3$, 9:1) gave solid (126 mg, 85%). $^1$HNMR (400 MHz, CDCl$_3$): 1.00 (t, J=7.2, 3H), 1.44 (d, J=9.2, 9H), 2.05–2.25 (m, 2H), 2.95 (s, 3H), 4.03–4.32 (AB system, 2H), 5.30 (s, 2H), 5.32–5.43 (A of AB system, 1H), 5.68–5.73 (B of AB system, 1H), 7.19, 7.37 (ss, 1H), 7.63–7.69 (m, 1H), 7.80–7.85 (m, 1H), 7.94 (t, J=8.4, 1H), 8.16–8.25 (dd, J=29.2, J=8.4, 1H), 8.38 (d, J=13.2, IH).

Camptothecin-20-O-ester of N-tert-butoxycarbonylmethylglycine (100 mg, 0.19 mmol) were dissolved in dichloromethane and trifluoracetic acid, then stirred 30 min. at room temperature. The yellow solution was concentrated under high vacuum. Recrystalization by methanol and ethyl ether obtained solid 96 mg, yield 94%. $^1$HNMR (400 MHz, DMSO): 0.96 (t, J=7.23H), 2.10–2.22 (m, 2H), 2.61 (s, 3H), 4.28–4.50 (AB system, 2H), 5.27–5.38 (AB system, 2H), 5.56 (s, 2H), 7.27 (s, 1H), 7.74 (t, J=7.6, 1H), 7.88 (t, J=7.6, 1H), 8.14–8.17 (d, J=9.6, 2H), 8.73 (s, 1H), 9.15 (brs, 1H); $^{13}$CNMR (400 MHz, DMSO): 7.56, 30.13, 32.53, 47.88, 50.31, 66.39, 77.71, 95.30, 118.85, 127.84, 128.04, 128.67, 128.78, 129.83, 130.60, 131.75, 144.58, 146.17, 147.90, 152.33, 156.50, 166.10, 166.82

EXAMPLE 3

Conversion of camptothecin and SN-38 20(S) ω aminoalkanoanic esters to lactam, ortho lactone and acetic acid Prodrugs The procedure involves placing in solution a 20-OR ω-aminoalkanoanic ester of camptothecin or SN-38, in which R=CO[CH$_2$]$_n$NH$_2$ and n=1–3. The basic amino group of the prodrug serves three roles. First, at pH ranges of 3 to 5, it enhances aqueous solubility. Second, it enhances responsiveness to a transmembrane ammonium sulfate gradient across the liposomal bilayer, thereby facilitating active loading of the agent into the liposomal aqueous core. Third, at a physiological pH of 7 or above (the pH to be encountered following drug release at the tumor site), the nucleophilicity of the amine manifests itself and cyclization to the C-21 carbonyl carbon occurs. This cyclization triggers a rapid and convenient non-enzymatic decomposition process that releases active camptothecin.

In contrast to 10-OR-CPT-20-OH compounds such as CPT-11, which are known to exhibit hydrolysis-resistant carbamate bonds that require enzymatic cleavage, reversed-phase high performance liquid chromatographic (RP-HPLC) studies of the stabilities of several 10-OH-CPT-20-OR and CPT-20-OR glycinate ester prodrugs (where R=COCH$_2$NH$_2$) revealed extensive chemical (i.e. non-enzymatic) decomposition in every case (CPT and SN-38 glycinate esters were studied). Prodrug decomposition was observed in phosphate buffered saline (PBS) at pH 7.4, as well as in human plasma and blood.

The presence of the amine functionality was found to be essential for the prodrug decomposition. Whereas camptothecin-20(S)-glycinate 1 [1 μM, PBS (pH 7.4), 37° C.] underwent extensive decomposition (~90%) within 3 hours, its corresponding aliphatic ester analog camptothecin-20(S)-acetate (differing solely by the replacement of the amino group with a proton) demonstrated excellent stability in the above fluids for days with negligible evidence of hydrolysis. Amine-containing esters of camptothecin with longer alkyl functionalities (R=COCH$_2$CH$_2$NH$_2$, R=COCH$_2$CH$_2$CH$_2$NH$_2$) also reacted under similar conditions, albeit at a slower rate (half-lifes of 26.4 hr and 36.7 hr, respectively) than their glycinate counterparts.

To better understand the mechanism of pro drug decomposition, RP-HPLC coupled with electrospray ionization-tandem mass spectrometry (ESI-MS/MS) and $^{13}$C, $^{15}$N, and 2D NMR experiments were used to study the decomposition reaction of camptothecin-20(S)-glycinate. Camptothecin-20(S)-glycinate 1 decomposed to produce several products: the closed-ring lactone form of camptothecin 5, the ring-opened carboxylate form of camptothecin 6, and two novel decomposition products 3 and 4 generated following the formation of an unusual six membered morpholine 2,5-dione ring 2 (or lactam intermediate).

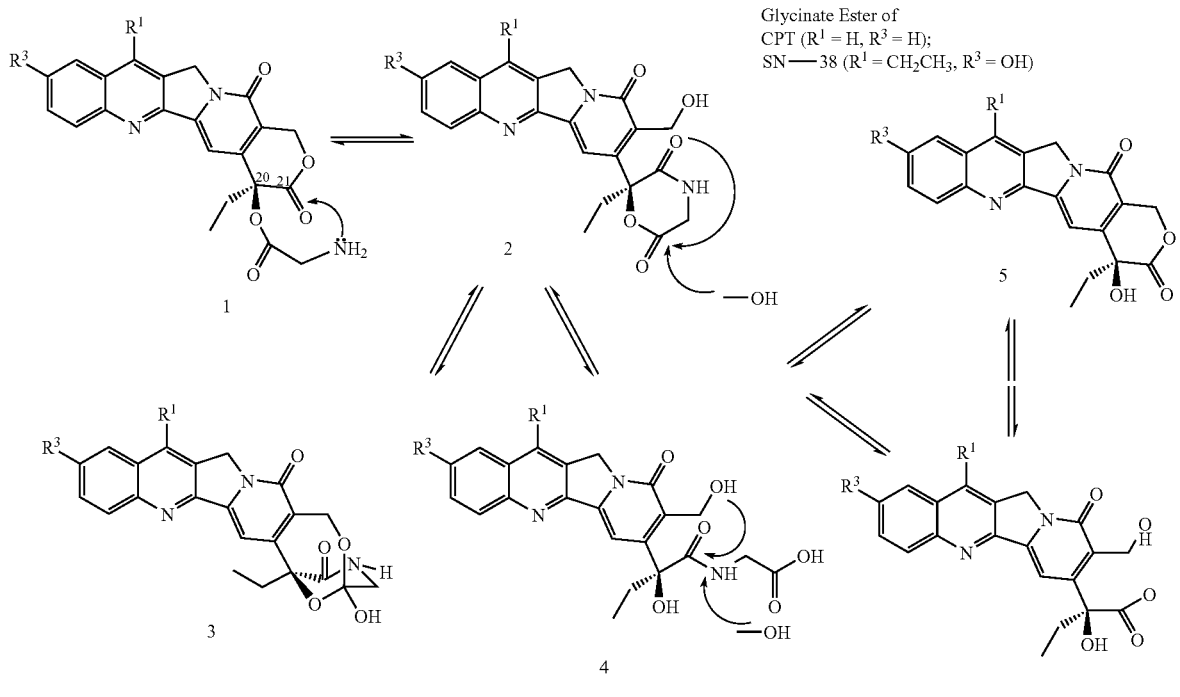

The lactam intermediate arose by intramolecular nucleophilic attack of the amino group on the lactone E-ring carbonyl carbon of camptothecin and is in fast equilibrium with structures 3 (which we refer to as the ortho lactone) and 4. Ortho lactone 3 arose by a second intramolecular reaction within the lactam intermediate and 3 exhibited the same mass as camptothecin-20(S)-glycinate ester but with a strikingly different fragmentation pattern. 4 arose by a competitive intermolecular reaction to the lactam intermediate and reacted to release both 5 and 6. HPLC-ESI-MS full scan showed the mass values for the protonated molecular (MH$^+$) ions of camptothecin glycinate ester degradation products were: 1 (406), 3 (406), 4 (424), 5 (349), 6 (389).

MS/MS showed that CPT glycinate ester 1 and CPT ortho lactone 3 were isomers with different fragmentation pattern. CPT glycinate fragmentation pattern [m/z(%)] was: 406 (25%), 331 (100%), 303 (30%); CPT ortho lactone fragmentation pattern was: 406 (100%), 388 (40%), 303 (20%). Likewise, N-substituted glycinate ester analogs of other camptothecins (1 µM, in PBS, pH 7.4), including SN-38, underwent extensive decomposition (~90%) within 3 hours. HPLC data for each analog studied was consistent with the generation of the novel decomposition products, along with the lactone and carboxylate forms of the parent drug. ESI-MS/MS analysis indicated that the proposed ortho lactone 3 generated for N-methyl CPT glycinate ester displayed the same mass as the ester but with a different fragmentation pattern. HPLC-ESI-MS full scan showed the mass values for the protonated molecular (MH$^+$) ions of N-methyl camptothecin glycinate ester degradation products were: 1 (420), 3 (420), 4 (438), 5 (349), 6 (389). MS/MS showed that N-methyl CPT glycinate ester 1 and CPT N-methyl ortho lactone 3 were isomers with different fragmentation pattern. N-methyl CPT glycinate fragmentation pattern [m/z(%)] was: 420 (86%), 331 (100%), 303 (30%); CPT N-methyl ortho lactone fragmentation pattern was: 420 (100%), 402 (50%), 303 (37%). As in the case for the camptothecin glycinate ester, the novel degradation products were generated from the proposed lactam intermediate. Further evidence for proposed degradation products 3 and 4 includes: (1) Glycine carbonyl $^{13}$C isotopic labeling NMR experiment in PBS showing that this carbon exists as a tetrahedral carbon as in 3. (2) Glycine $^{15}$N isotopic labeling NMR experiments showing that 3 and 4 have amide bonds. (3) 2D NMR spectrum of isolated N-methyl camptothecin ortho lactone 3

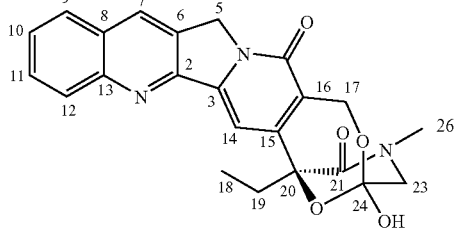

| Atom | DMSO (ppm) | | |
|---|---|---|---|
| # | $\delta_C$ | $\delta_H$ | Observed Coupling |
| 2 | 152.8 | — | $^3J_{CH}$ H-5, H-7, H-14 |
| 3 | 142.7 | — | $^2J_{CH}$ H-14; $^5J_{CH}$ H-17b |
| 5 | 50.0 | 5.26(2H) | $^3J_{CH}$ H-7 |
| 6 | 129.8 | — | $^2J_{CH}$ H-5 |
| 7 | 131.5 | 8.66(1H) | $^3J_{CH}$ H-5, H-9 |
| 8 | 127.5 | — | — |
| 9 | 128.5 | 8.08(1H) | $^3J_{CH}$ H-7 |
| 10 | 127.8 | 7.69(1H) | $^3J_{CH}$ H-12 |
| 11 | 130.3 | 7.86(1H) | $^3J_{CH}$ H-9 |
| 12 | 129.0 | 8.17(1H) | $^3J_{CH}$ H-10 |
| 13 | 147.9 | — | $^3J_{CH}$ H-7, H-9, H-11 |
| 14 | 100.4 | 7.26(1H) | $^4J_{CH}$ H-17b |
| 15 | 150.6 | — | $^3J_{CH}$ H-19b, H-17a |
| 16 | 128.2 | — | $^2J_{CH}$ H-17a, H-17b; $^3J_{CH}$ H-14 |
| 17 | 57.4 | 4.83(1H, a), 5.03(1H, b) | — |
| 18 | 7.9 | 0.92(3H) | $^2J_{CH}$ H-19a, H-19b |
| 19 | 33.1 | 2.05(1H, a), 2.35(1H, b) | $^2J_{CH}$ H-18 |
| 20 | 82.0 | — | $^2J_{CH}$ H-19a, H-19b; $^3J_{CH}$ H-14, H-1 |
| 21 | 166.6 | — | $^3J_{CH}$ H-19a, H-26; $^6J_{CH}$ H-17b |
| 23 | 54.8 | 3.41(1H, a), 3.71(1H, b) | $^3J_{CH}$ H-26, OH |
| 24 | 107.1 | — | $^2J_{CH}$ H-23a, H-23b, OH; $^3J_{CH}$ H-17 H-17b; $^4J_{CH}$ H-26 |
| 26 | 34.1 | 2.85(3H) | $^3J_{CH}$ H-23a |
| OH | — | 8.06(1H) | — |

EXAMPLE 4

Procedure for the Isolation of the ortho lactone from CPT-N-methyl glycinate

Camptothecin N-methyl glycinate trifluoroacetic acid salt was dissolved in DMF, 1.2 eq. triethylamine was then added and reaction stirred overnight at room temperature. Organic solvent was removed and a yellow precipitate was rinsed with water, filtered, and dried under vacuum. Yield: 98%.

EXAMPLE 5

Procedure for the Isolation of the ortho lactone from SN-38 methyl glycinate ester SN-38 N-methyl glycinate trifluoroacetic acid salt was dissolved in unhydrous DMF, 1.5 eq. triethylamine was then added and reaction stirred overnight at room temperature. Organic solvent was removed and residue was rinsed with water to remove salt, SN-38 N-methyl ortho lactone was extracted with ethyl acetate.

EXAMPLE 6

Procedure for the Isolation of the ortho lactone from 9-NC-methyl glycinate ester 9-Nitro Camptothecin N-methyl glycinate hydrocholoride was dissolved in DMF, 1.5 eq. triethylamine was then added and reaction stirred overnight at room temperature. Organic solvent was removed and residue was dried under vacuum.

EXAMPLE 7

Procedure for the Isolation of the Ortho Lactone from 10,11-MDCPT-20-glycinate ester 10,11-methylenedioxy Camptothecin N-methyl glycinate hydrocholoride was dissolved in anhydrous dichloromethane, 1.5 eq. triethylamine was added and reaction stirred overnight at room temperature. Organic solvent was removed and residue was rinsed with water and dried under vacuum.

EXAMPLE 8

LC/MS Condition for Elucidation of Degradation Products of Camptothecin-20(S)-Glycinate in Aqueous Solution The LC/MS system consisted of an HP 1100 HPLC equipped with a 50×1.0 mm i.d. (3 micron) Luna C18 microbore column (Phenomex, Torrence, Calif.). Isocratic separations were preformed at 35 uL/min using 80% acetonitrile and 20% 10 mM ammonium formate pH 5.5. Salts in the samples were diverted from the mass spectrometer during the first two minutes of each experiment. Electrospray mass spectra were acquired on a Finnigan LCQ Classic (San Jose, Calif.) quadrupole ion trap mass spectrometer in the positive ion mode. Standard electrospray conditions were used (spray voltage 4.5 kV, shealth gas flow rate 60 arb. units, and capillary temp. 225° C.). Full scan mass spectra were obtained over a range of 100 to 1000 m/z. Typical tandem mass spectra parameters were 3 m/z isolation width, 35% normalized collision energy, $q_z$=0.25 and CID time of 30 ms.

EXAMPLE 9

Remote "active" loading of prodrug into premade small unilamellar vesicles, with diameters of 100 nm, was carried out by using transmembrane ammonium sulfate gradients. Prodrug was added to a liposomal suspension where initially $[(NH_4)_2SO_4]_{CORE}$. $[(NH_4)_2SO_4]_{EXTERNAL}$; loading of the prodrug occurred as a result of base exchange (initiated by $NH_3$ gas molecules departing the liposome). Whereas underivatized camptothecin and DB-67 localize predominantly in the bilayer compartment of the liposome, their 20-OR prodrugs, where R) $CO[CH_2]_nNH\ 2$ and n) 1–3, loaded with high efficiency (60 to 90%) into the core of liposomes at clinically relevant drug-to-lipid ratios (between 1:4 to 1:20). More importantly, these core-loaded liposomal formulations of camptothecin 4-aminobutanoate ester and DB-67 4-aminobutanoate ester exhibited markedly improved stabilities in whole blood relative to their free forms. Whereas the decomposition of free prodrug in both cases was extensive, liposomal entrapment prevented the degradation process from occurring, providing indirect evidence that the prodrug was effectively retained within the liposome for periods up to 40 h. These time periods are known to be sufficient for successful tumor-targeting to be achieved.

What is claimed:

1. A compound with the formula:

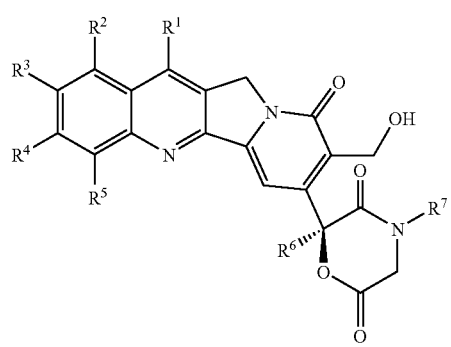

where $R^1$ may be: a) hydrogen, a halogen atom, a branched or linear alkyl group, a branched or linear alkenyl group, a branched or linear alkynyl group, a cycloalkyl group, a cycloalkenyl group, an alkoxy group, an alkylamino group, a dialkylamino group, an alkylthiol group, a thiol group, a phenyl group, an amino group, a nitro group, a cyano group; b) a $(CH^2)_YNR^8R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate;

$R^2$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group; b) a $(CH_2)_YNR^8\ R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate;

$R^3$ may be: a) hydrogen, a halogen atom, a linear or branched alkyl group, a linear or branched alkenyl group, a linear or branched alkynyl group, an amino group, an alkylamino group, a dialkylamino group, a nitro group, a $C_{3-10}$ cycloalkyl group, a $C_{3-10}$ cycloalkenyl group, a $C_{8-10}$ cycloalkynyl group, a thiol group, a cyano group, a hydroxyl group; b) a $(CH_2)_YNR^8R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate;

$R^4$ may be hydrogen, a halogen atom, a hydroxy group, an amino group, a methoxy group, an alkyl group, an alkynyl group or an alkenyl group;

$R^5$ may be hydrogen or fluorine;

$R^6$ may be an alkyl group, an alkenyl group, an alkynyl group, or a benzyl group;

$R^7$ may be hydrogen, an alkyl group, an alkenyl group, an alkynyl group, a benzyl group, an alkoxy group, an aryloxy group, or an acyloxy group; and pharmaceutically acceptable salts thereof.

2. A compound with the formula:

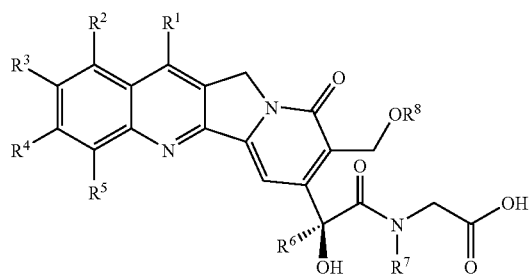

where $R^1$ may be: a) hydrogen, a halogen atom, a branched or linear alkyl group, a branched or linear alkenyl group, a branched or linear alkynyl group, a cycloalkyl group, a cycloalkenyl group, an alkoxy group, an alkylamino group, a dialkylamino group, an alkylthiol group, a thiol group, a phenyl group, an amino group, a nitro group, a cyano group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate;

$R^2$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate;

$R^3$ may be: a) hydrogen, a halogen atom, a linear or branched alkyl group, a linear or branched alkenyl group, a linear or branched alkynyl group, an amino group, an alkylamino group, a dialkylamino group, a nitro group, a 3–10 membered heterocyclic ring, a $C_{3-10}$ cycloalkyl group, a $C_{3-10}$ cycloalkenyl group, a $C_{8-10}$ cycloalkynyl group, a thiol group, a cyano group, a hydroxyl group; b) a $(CH_2)_Y NR^8 R^9$ group, wherein Y is an integer from 1–10 and $R^8$ and $R^9$ are, independently, hydrogen, an alkyl group, an alkenyl group, an alkynyl group, an amine, an alkyl amine, a dialkyl amine, a hydroxy group, an alkoxy group, an acyl group, a carbamate;

$R^4$ may be hydrogen, a halogen atom, a hydroxy group, an amino group, a methoxy group, an alkyl group, an alkynyl group or an alkenyl group;

$R^5$ may be hydrogen or fluorine;

$R^6$ may be an alkyl group, an alkenyl group, an alkynyl group, a benzyl group, an alkoxy group, an aryloxy group, or an acyloxy group;

$R^7$ may be hydrogen, an alkyl group, an alkenyl group, a benzyl group, an alkoxy group, an aryloxy group, or an acyloxy group; and $R^8$ may be hydrogen, an alkyl group, or an alkenyl group; and pharmaceutically acceptable salts thereof.

* * * * *